(12) United States Patent
Yamada

(10) Patent No.: US 11,571,158 B2
(45) Date of Patent: Feb. 7, 2023

(54) ELECTRODE AND BIOSIGNAL MEASURING DEVICE

(71) Applicant: FUJIFILM Business Innovation Corp., Tokyo (JP)

(72) Inventor: Wataru Yamada, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 413 days.

(21) Appl. No.: 16/869,549

(22) Filed: May 7, 2020

(65) Prior Publication Data

US 2021/0161417 A1 Jun. 3, 2021

(30) Foreign Application Priority Data

Nov. 28, 2019 (JP) .............................. JP2019-215713

(51) Int. Cl.
*A61B 5/291* (2021.01)
*A61B 5/00* (2006.01)

(52) U.S. Cl.
CPC ............ *A61B 5/291* (2021.01); *A61B 5/6815* (2013.01); *A61B 5/6817* (2013.01); *A61B 2562/0209* (2013.01); *A61B 2562/0285* (2013.01); *A61B 2562/164* (2013.01)

(58) Field of Classification Search
CPC ..... A61B 5/291; A61B 5/6815; A61B 5/6817; A61B 2562/0209; A61B 2562/0285; A61B 2562/164
See application file for complete search history.

(56) References Cited

U.S. PATENT DOCUMENTS

| | | | |
|---|---|---|---|
| 2015/0044656 A1* | 2/2015 | Eichhorn | A61B 5/11 600/587 |
| 2016/0121100 A1* | 5/2016 | Crone | A61N 1/0492 607/142 |
| 2017/0188859 A1* | 7/2017 | Banet | A61B 5/6826 |
| 2017/0281086 A1* | 10/2017 | Donaldson | A61B 5/14542 |

FOREIGN PATENT DOCUMENTS

| | | | | |
|---|---|---|---|---|
| JP | 2011-217986 | | 11/2011 | |
| JP | 2011217986 A | * | 11/2011 | ........... A61B 5/0408 |
| JP | 2016163688 | | 9/2016 | |
| JP | 2016163688 A | * | 9/2016 | ........... A61B 5/0408 |
| KR | 20160024903 A | * | 3/2016 | ........... A61B 5/0476 |
| WO | 2016136629 | | 9/2016 | |
| WO | WO-2016136629 A1 | * | 9/2016 | ........... A61B 5/0478 |

* cited by examiner

*Primary Examiner* — Oyesola C Ojo
(74) *Attorney, Agent, or Firm* — JCIPRNET

(57) ABSTRACT

An electrode includes a living body contact portion that is to be in contact with a living body and that contains a rubber material and at least one carbon material selected from carbon nanotubes and graphene. The ratio of the volume resistivity of the living body contact portion to the surface resistivity of the living body contact portion is 1.2 or more. The amount of the carbon material in the living body contact portion is 3 parts by mass or more and 20 parts by mass or less relative to 100 parts by mass of the rubber material, or the living body contact portion has a 25% compression hardness of 20 kPa or more and 110 kPa or less.

11 Claims, 4 Drawing Sheets

ELECTRODE AND BIOSIGNAL MEASURING DEVICE

CROSS-REFERENCE TO RELATED APPLICATIONS

This application is based on and claims priority under 35 USC 119 from Japanese Patent Application No. 2019-215713 filed Nov. 28, 2019.

BACKGROUND

(i) Technical Field

The present disclosure relates to an electrode and a biosignal measuring device.

(ii) Related Art

A biological electrode (an example of "electrodes") is used as a member for detecting biosignals.

For example, Japanese Unexamined Patent Application Publication No. 2016-163688 discloses a brainwave measuring electrode including a base material formed of an elastic body and a structure formed on the surface of the base member. The base material includes a protrusion having a contact surface to be in contact with the head skin. The structure contains plural nanocarbon materials. The plural nanocarbon materials are connected to each other to form a network structure and fixed to the surface of the base member.

Japanese Unexamined Patent Application Publication No. 2011-217986 discloses an ear canal insertable electrode that can be inserted into the human ear canal. The ear canal insertable electrode includes an elastic body that deforms according to the shape of the ear canal, an electrically conductive layer that covers at least part of the surface of the elastic body and is electrically connected to a conducting wire, and an electrically conductive flexible layer that covers the surface of the electrically conductive layer, has higher electrical resistivity than the electrically conductive layer, and deforms according to the shape of the ear canal. The ear canal insertable electrode has an outer circumferential surface which will contact the inner circumferential surface of the ear canal to make an electrical connection with the ear canal due to the contact pressure therebetween.

SUMMARY

Aspects of non-limiting embodiments of the present disclosure relate to an electrode (hereinafter also referred to as a "specific electrode") including a living body contact portion that is to be in contact with a living body and that contains a rubber material and at least one carbon material selected from carbon nanotubes and graphene. The specific electrode has good shape conformability and accurately measures biosignals compared with a specific electrode in which the amount of the carbon material is less than 3 parts by mass or more than 20 parts by mass relative to 100 parts by mass of the rubber material, or the ratio of the volume resistivity of the living body contact portion to the surface resistivity of the living body contact portion is less than 1.2.

Aspects of non-limiting embodiments of the present disclosure also relate to a specific electrode that has good shape conformability and accurately measures biosignals compared with a specific electrode that has a 25% compression hardness of less than 20 kPa or more than 110 kPa or in which the ratio of the volume resistivity of the living body contact portion to the surface resistivity of the living body contact portion is less than 1.2.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an electrode including a living body contact portion that is to be in contact with a living body and that contains a rubber material and at least one carbon material selected from carbon nanotubes and graphene. The ratio of the volume resistivity of the living body contact portion to the surface resistivity of the living body contact portion is 1.2 or more. The amount of the carbon material in the living body contact portion is 3 parts by mass or more and 20 parts by mass or less relative to 100 parts by mass of the rubber material, or the living body contact portion has a 25% compression hardness of 20 kPa or more and 110 kPa or less.

BRIEF DESCRIPTION OF THE DRAWINGS

Exemplary embodiments of the present disclosure will be described in detail based on the following figures, wherein.

DETAILED DESCRIPTION

Figure 1:
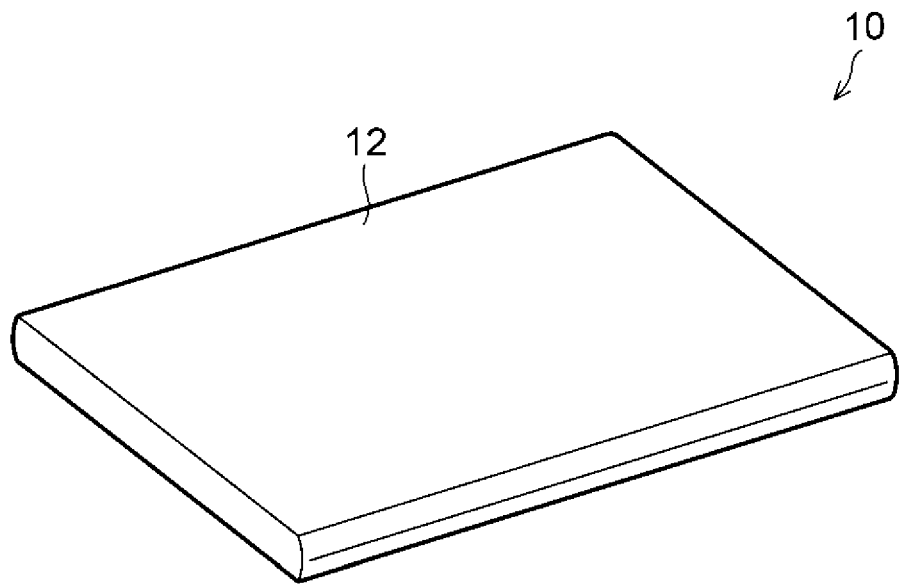
FIG. 1 is a schematic perspective view of one example of a biological electrode according to an exemplary embodiment.

Hereinafter, a "first exemplary embodiment" and a "second exemplary embodiment" of an electrode which is an example of the present disclosure will be described in detail. The following description and Examples are provided to illustrate exemplary embodiments but are not intended to limit the scope of the exemplary embodiments. The "first exemplary embodiment" and the "second exemplary embodiment" of the electrode according to the present disclosure are also collectively referred to as "exemplary embodiments".

The upper limit or lower limit of one numerical range in stepwise numerical ranges in the present disclosure may be replaced by the upper limit or lower limit of another stepwise numerical range. The upper limit or lower limit of any numerical range described in the present disclosure may be replaced by the values described in Examples.

In the present disclosure, each component may contain multiple corresponding substances. In the present disclosure, the amount of each component in a composition refers to, when there are multiple substances corresponding to each component in the composition, the total amount of the substances present in the composition, unless otherwise specified.

Electrode

First Exemplary Embodiment

When the electrode according to the present disclosure is a first exemplary embodiment, the electrode includes a living body contact portion that is to be in contact with a living body and that contains a rubber material and at least one carbon material selected from carbon nanotubes and graphene, wherein the amount of the carbon material is 3 parts by mass or more and 20 parts by mass or less relative to 100 parts by mass of the rubber material, and the ratio of the volume resistivity of the living body contact portion to the surface resistivity of the living body contact portion is 1.2 or more.

Second Exemplary Embodiment

When the electrode according to the present disclosure is a second exemplary embodiment, the electrode includes a living body contact portion that is to be in contact with a living body and that contains a rubber material and at least one carbon material selected from carbon nanotubes and graphene, wherein the living body contact portion has a 25% compression hardness of 20 kPa or more and 110 kPa or less, and the ratio of the volume resistivity of the living body contact portion to the surface resistivity of the living body contact portion is 1.2 or more.

In the electrode according to the exemplary embodiment, at least the living body contact portion to be in contact with a living body has the above features, or the electrode may generally have the above features.

The above features may allow the electrode according to the exemplary embodiment to have good shape conformability and accurately measure biosignals. The reasons for this are assumed as described below.

An electrode (also referred to as a "biological electrode") for measuring a microcurrent that flows from the skin surface of a living body is used to measure biosignals, such as brainwaves, heart rate, and pulse. To accurately measure biosignals, at least the living body contact portion of the biological electrode needs to have low resistance and good deformability (i.e., shape conformability) in accordance with changes in the shape of the living body.

To reduce the resistance of the living body contact portion of the biological electrode, the addition of metal powder or carbon material, such as carbon black, as a conductive agent is known to be effective. However, metal power and carbon material, such as carbon black, also function as a reinforcing material and thus, when added to reduce the resistance, may increase the hardness of the living body contact portion to lower the shape conformability of the living body contact portion.

In the electrode according to the exemplary embodiment, at least the living body contact portion contains a rubber material and a carbon material. The carbon material is at least one selected from carbon nanotubes and graphene.

In the electrode according to the first exemplary embodiment, the presence of 3 parts by mass or more and 20 parts by mass or less of the carbon material relative to 100 parts by mass of the rubber material contributes to a reduction in the resistance of the living body contact portion although the carbon material is present in a small amount. This allows the living body contact portion to have low resistance without excessively increasing the hardness of the living body contact portion.

In the electrode according to the second exemplary embodiment, a 25% compression hardness in the range of 20 kPa or more and 110 kPa or less may contribute to good shape conformability of the living body contact portion, and the presence of at least one carbon material selected from carbon nanotubes and graphene lowers the resistance of the living body contact portion.

In light of the foregoing, the electrode according to the exemplary embodiment may have good shape conformability and accurately measure biosignals.

The electrode according to the exemplary embodiment will be described below in detail.

The electrode according to the exemplary embodiment is, for example, a sheet-shaped electrode as illustrated in FIG. 1.

The sheet-shaped electrode is, for example, a monolayer structure formed of a layer-shaped living body contact portion. The sheet-shaped electrode may be a structure having two or more layers including a base member and a layer-shaped living body contact portion on the base member. In other words, the electrode may be a structure generally composed of a living body contact portion or may be a structure including a living body contact portion and a member (e.g., a base member that supports the living body contact portion) other than the living body contact portion.

The shape of the electrode according to the exemplary embodiment is not limited and selected according to the application. For example, the electrode may be a structure including a base member and a living body contact portion disposed on the surface of the base member and having plural protrusions (see FIG. 2).

Figure 2:
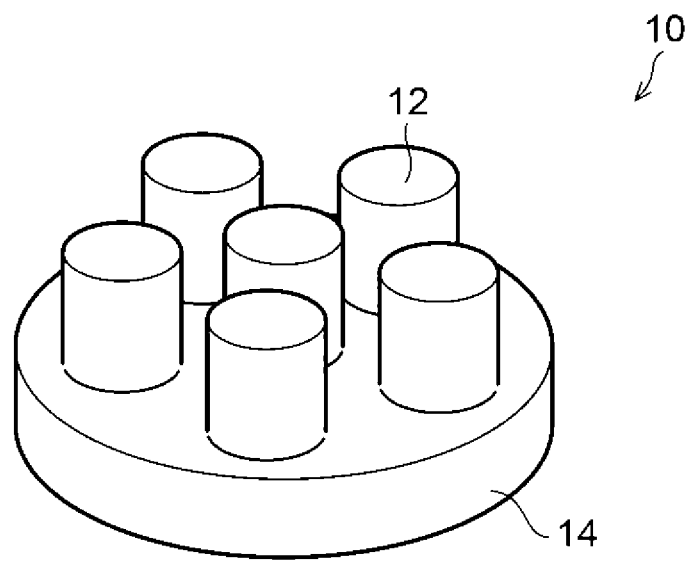
FIG. 2 is a schematic perspective view of another example of the biological electrode according to the exemplary embodiment.

In FIG. 1 and FIG. 2, the reference numeral 10 denotes an electrode, 12 a living body contact portion, and 14 a base member.

Living Body Contact Portion

The electrode according to the exemplary embodiment has a living body contact portion to be in contact with a living body. In the exemplary embodiment, the living body refers to a part of the human body or other creature's body and includes the skin and other body tissues. Examples of specific body parts include the head including the ears, the eyes, the mouth, and the nose; the neck; the upper extremities including the hands, the upper arms, the axillae, the forearms, the thorax, and the abdomen; and the lower extremities including the thighs, the knees, the shins, the ankles, the legs, and the toes.

The shape of the living body contact portion is not limited and may have plural protrusions as described above or may be appropriately selected according to, for example, the shape of the living body to be in contact with the living body contact portion.

The living body contact portion may have a surface layer to be in contact with the living body and a base layer in contact with the surface layer. In the exemplary embodiment, the surface layer may have a larger carbon material content than the base layer in order to improve the shape conformability and accurately measure biosignals. In the living body contact portion, the surface layer refers to a section ranging from the surface to be in contact with the living body to a thickness of 500 μm. The base layer refers to a section being in contact with the surface layer and ranging from the surface to a thickness of more than 500 μm.

Next, the structure of the living body contact portion of the electrode according to the exemplary embodiment will be described in detail. In the description, the living body contact portion of the electrode according to the exemplary embodiment is referred to simply as a living body contact portion.

The living body contact portion contains a rubber material and at least one carbon material selected from carbon nanotubes and graphene. The living body contact portion may contain other additives.

The living body contact portion may be made of foam or made of non-foam. The living body contact portion may be made of foam containing a rubber material and a carbon material.

Rubber Material

Examples of the rubber material include epichlorohydrin rubber, urethane rubber, nitrile rubber, isoprene rubber, butadiene rubber, epichlorohydrin-ethylene oxide rubber, ethylene-propylene-diene rubber (EPDM), styrene-butadiene rubber (SBR), chlorinated polyisoprene, acrylonitrile-butadiene rubber (NBR), chloroprene rubber, hydrogenated polybutadiene, butyl rubber, silicone rubber, and the like, and a mixed material of two or more of these rubbers. Examples of the rubber material also include elastomers.

Among these, the rubber material may be urethane rubber, nitrile rubber, epichlorohydrin (ECO) rubber, ethylene-propylene-diene rubber (EPDM), or silicone rubber, and more preferably urethane rubber or silicone rubber in order to improve the shape conformability and accurately measure biosignals. In particular, silicone rubber may be used due to its high biosafety.

Carbon Material

The carbon material includes at least one selected from carbon nanotubes and graphene.

The carbon nanotube (hereinafter referred to as a "CNT") used in the exemplary embodiment is, for example, a tube-shaped material having a maximum diameter of 1 μm or less. The applicable length of the CNT is not limited, but typically preferably in the range of from 10 nm to 1000 μm, and more preferably in the range of from 100 nm to 300 μm. The diameter (thickness) of the CNT is not limited, but typically in the range of from 1 nm to 1 μm, and more preferably in the range of from 3 nm to 500 nm. An ideal CNT is a tube formed of a sheet-shaped structure (graphene sheet) composed of carbon atoms arranged in a hexagonal lattice, where the graphene sheet is parallel to the axis of the tube. This tube may be formed of a multilayer graphene sheet.

Graphene used in the exemplary embodiment is particles of a two-dimensional thin film with a honeycomb structure composed of a monolayer or multilayer of carbon (C) atoms. Graphene preferably has an average particle size of 0.1 μm to 50 μm and an average flake thickness of 1 nm to 50 nm, and more preferably has an average particle size of 1 μm to 50 μm and an average flake thickness of 5 nm to 25 nm.

The average particle size is a value calculated from the mean of the particle size of 50 particles present in a certain area through electron microscopic observation, where the particle size of each particle is obtained as the diameter of a circle having the same projected area. The flake thickness refers to a maximum thickness of graphene measured in the thickness direction. In the exemplary embodiment, the average flake thickness is the mean of the flake thickness of 50 flaky particles present in a certain area through electron microscopic observation.

The amount of the carbon material (e.g., the total amount of carbon nanotube and graphene) used in the exemplary embodiment is preferably 3 parts by mass or more and 20 parts by mass or less, and more preferably 5 parts by mass or more and 15 parts by mass or less relative to 100 parts by mass of the rubber material in order to improve the shape conformability and accurately measure biosignals.

The total amount of carbon nanotube and graphene is preferably 90% by mass or more, more preferably 96% by mass or more, and still more preferably 98% by mass or more relative to the total mass of the carbon material.

The living body contact portion may contain electrically conductive materials, such as an electron-conductive agent other than carbon nanotubes and graphene, an ion-conductive agent, and an electrically conductive polymer as long as the shape conformability of the electrode and the accuracy of the biosignal measurement are improved. A combination of two or more of these electrically conductive materials may be contained and dispersed in the living body contact portion. By combining electrically conductive materials, the electrical resistance of the living body contact portion can be controlled. The total amount of these electrically conductive materials in the living body contact portion is preferably 5 parts by mass or less, more preferably 3 parts by mass or less, and still more preferably 1 part by mass or less relative to 100 parts by mass of the rubber material.

Examples of the electron-conductive agent other than carbon nanotubes and graphene include metals or alloys, such as carbon black, graphite, aluminum, nickel, and copper alloys; and metal oxides, such as tin oxide, zinc oxide, potassium titanate, tin oxide-indium oxide, and tin oxide-antimony oxide composite oxide.

Examples of the ion-conductive agent include various surfactants, such as sulfonic acid salts and ammonium salts; and various surfactants, such as cationic, anionic, and nonionic surfactants.

Examples of the electrically conductive polymer includes various (e.g., styrene) copolymers with meth(acylate) having a carboxyl group coupled to quaternary ammonium base, a polymer having a quaternary ammonium base, such as a copolymer of methacrylate and maleimide coupled to quaternary ammonium base, a polymer having an alkali metal salt of a sulfonic acid, such as poly(sodium sulfonate), a polymer having at least a hydrophilic unit of an alkyl oxide in the molecular chain, for example, polyethylene oxide, polyethylene glycol-polyamide copolymer, polyethylene oxide-epichlorohydrin copolymer, poly(ether-amide-imide), a block polymer having polyether as a main segment, polyaniline, polythiophene, polyacetylene, polypyrrole, and polyphenylenevinylene. These electrically conductive polymers can be used in the undoped state or the doped state.

Other Additives

Examples of other additives include foaming agents, flame retardants, anti-degradants, foam stabilizers, and various fillers.

Examples of foaming agents include benzenesulfonyl hydrazide, azodicarbonamide, N,N'-dinitrosopentamethylenetetramine, and a mixture thereof.

Examples of flame retardants include phosphoric ester compounds, such as tris(chloroethyl) phosphate and tris (chloropropyl) phosphate.

Examples of anti-degradants include antioxidants, such as phenolic antioxidants, amine antioxidants, phosphite antioxidants; ultraviolet absorbers, such as benzotriazole ultraviolet absorbers and benzophenone ultraviolet absorbers; and light stabilizers, such as hindered amine light stabilizers.

Examples of foam stabilizers include silicone surfactants, such as dimethyl silicone oil and polyether-modified silicone oil; and cationic surfactants, anionic surfactants, and amphoteric surfactants.

Examples of various fillers include silica and calcium carbonate.

In addition to the above additives, examples of other additives further include materials that may be added to the rubber material, such as softeners, plasticizers, curing agents, antioxidants, surfactants, coupling agents, and fillers (e.g., silica, calcium carbonate).

Examples of other additives also include the following additives.

Examples of vulcanizing agents for the rubber material include vulcanizing agents which causes vulcanization by removing a halogen group, such as sulfur, 2,4,6-trimercapto-s-triazine, and 6-methylquinoxaline-2,3-dithiocarbamate.

Examples of vulcanization accelerators for the rubber material include thiazole, sulfenamide, thiuram, dicarbamate, and xanthate vulcanization accelerators. These may be used alone or in combination of two or more. In addition, known rubber compounding materials, such as zinc oxide and stearic acid, can be added.

Examples of platinum catalysts for cross-linking of silicone rubber include platinum-based catalysts, such as chloroplatinic acid, alcohol solution of chloroplatinic acid, a reaction product of chloroplatinic acid with an alcohol, a reaction product of chloroplatinic acid with an olefin compound, a reaction product of chloroplatinic acid with vinyl group-containing siloxane, platinum-olefin complex, and platinum-vinyl group-containing siloxane complex; and platinum group metal-based catalysts, such as rhodium complexes and ruthenium complexes. These catalysts dissolved or dispersed in alcohol solvents, hydrocarbon solvents, or siloxane solvents may be used.

When addition cure silicone resin is used, an addition reaction controlling agent may be added. The addition reaction controlling agent is added as a quencher for inhibiting the action of a platinum catalyst in a solution and in a low-temperature environment before heat curing after coating film formation. Specific examples of the addition reaction controlling agent include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, and 1,1,3,3-tetramethyl-1,3-divinyldisiloxane.

Examples of photo-curing methods include a method involving using a resin having a (meth)acrylate terminal or an olefin terminal or adding a cross-linking agent whose terminal is (meth)acrylate, olefin, or a thiol group while adding a photo-radical generator for generating radicals upon light irradiation; and a method involving using a resin or cross-linking agent having an oxirane group, an oxetane group, and a vinyl ether group and adding a photoacid generator for generating acid upon light irradiation.

Examples of photo-radical generators include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxol-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

Curing can also be performed by addition of a thermally decomposable radical generator. Examples of the thermal radical generator include 2,2'-azobis(isobutyronitrile), 2,2'-azobis(2,4-dimethylvaleronitrile), 2,2'-azobis(2-methylbutyronitrile), 4,4'-azobis(4-cyanovaleric acid), 2,2'-azobis(methylpropionamidine)hydrochloric acid, 2,2'-azobis[2-(2-imidazolin-2-yl)propane]hydrochloric acid, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutyrate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dimethyl-2,2'-azobis(2-methylpropionate), and dicumyl peroxide.

Examples of the photoacid generator include sulfonium salts, iodonium salts, sulfonyl diazomethane, N-sulfonyloxyimide, and oxime-O-sulfonate acid generator.

Properties of Living Body Contact Portion

Regarding the living body contact portion used in the exemplary embodiment, the ratio of the volume resistivity of the living body contact portion to the surface resistivity of the living body contact portion is 1.2 or more. To provide an electrode that has good shape conformability and that accurately measures biosignals, the ratio of the volume resistivity of the living body contact portion to the surface resistivity of the living body contact portion is preferably 1.5 or more, and more preferably 4.0 or more.

The values of the physical properties of the living body contact portion are measured in accordance with the following methods.

To provide an electrode that has good shape conformability and that accurately measures biosignals, the surface resistivity of the living body contact portion is preferably $1 \times 10^5 \Omega/\square$ or less, and more preferably $1 \times 10^3 \Omega/\square$ or less.

From the same viewpoint, the surface resistivity of the surface layer in the living body contact portion is preferably $1 \times 10^5 \Omega/\square$ or less, and more preferably $1 \times 10^3 \Omega/\square$ or less, and the surface resistivity of the base layer in the living body contact portion is preferably $1 \times 10^2 \Omega/\square$ or more and $1 \times 10^{10} \Omega/\square$ or less, and more preferably $1 \times 10^3 \Omega/\square$ or more and $1 \times 10^7 \Omega/\square$ or less.

Surface Resistivity

The surface resistivity of the living body contact portion is measured in accordance with the following method.

A sheet-shaped test sample is taken from the living body contact portion. The surface resistivity is measured by applying a voltage of 100 V to the test sample for 3 seconds. Specifically, the surface resistivity ($\Omega/\square$) of a surface of the living body contact portion to be in contact with a living body is measured at total 18 points, which are 6 points at regular intervals in the longitudinal direction of the test sample multiplied by 3 points at the center and the edges in the width direction, at a voltage of 100 V and a pressure of 1 kgf for an application time of 3 seconds by using a micro-current meter (R8430A available from Advantest Corporation) as a resistance meter and using a UR probe (available from Mitsubishi Chemical Analytech Co., Ltd.) as a probe. The mean of the surface resistivity is calculated.

The surface resistivity is measured in an environment with a temperature of 22° C. and a humidity of 55% RH.

Volume Resistivity

To provide an electrode that has good shape conformability and that accurately measures biosignals, the volume resistivity of the living body contact portion is preferably $1 \times 10^5 \Omega \cdot cm$ or less, and more preferably $1 \times 10^3 \Omega \cdot cm$ or less.

The volume resistivity of the living body contact portion is measured in accordance with the following method.

A sheet-shaped test sample is taken from the living body contact portion. A voltage adjusted so as to obtain an electric field (applied voltage/composition sheet thickness) of 1000 V/cm is applied to the test sample for 30 seconds by using a measurement jig (R12702A/B resistivity chamber available from Advantest Corporation) and a high resistance meter (R8340A digital high resistance/micro-current meter available from Advantest Corporation) in accordance with JIS K 6911:1995. The volume resistivity is calculated from the current that flows at this voltage in accordance with the following formula.

$$\text{Volume resistivity}(\Omega cm) = (19.63 \times \text{applied voltage} (V)) / (\text{current}(A) \times \text{test sample thickness (cm)})$$

25% Compression Hardness

To provide an electrode that has good shape conformability and that accurately measures biosignals, the 25% compression hardness of the living body contact portion is preferably 20 kPa or more and 110 kPa or less, more preferably 30 kPa or more and 80 kPa or less, and still more preferably 35 kPa or more and 65 kPa or less.

The 25% compression hardness of the living body contact portion is measured by the method in accordance with ASTM d1056.

Rubber Hardness

To provide an electrode that has high fitness to the living body and brings comfortable wearing feeling, the rubber hardness of the living body contact portion is preferably 20° or more and 80° or less, more preferably 30° or more and 60° or less, and still more preferably 35° or more and 55° or less.

The rubber hardness of the living body contact portion is measured in accordance with the following method.

The rubber hardness of the living body contact portion is the Shore A hardness. The Shore A hardness is measured in accordance with JIS K 6253-3:2012. Specifically, the hardness after an indenter point of a Type-A durometer is pressed against the sample for 15 seconds is measured as the rubber hardness (i.e., the Shore A hardness).

Surface Roughness Rz

To provide an electrode that has high fitness to the living body and brings comfortable wearing feeling, the surface roughness Rz of the living body contact surface in the living body contact portion is preferably 5 μm or more and 50 μm or less, and more preferably 10 μm or more and 40 μm or less.

The surface roughness Rz of the surface of the charging member is the ten-point average roughness Rz defined in JIS B 0601:1994.

The surface roughness Rz is obtained by measuring the surface roughness at 3 points of a measurement target by using a surface roughness measuring instrument (SURF-COM 1400A available from Tokyo Seimitsu Co., Ltd.) under the conditions of a cutoff of 0.8 mm, a measurement length of 4.0 mm, and a traverse speed of 0.3 mm/sec, and calculating the mean of the surface roughness.

Method for Manufacturing Living Body Contact Portion

The method for manufacturing the living body contact portion is not limited.

The living body contact portion is manufactured by, for example, extruding, using an extruder or the like, a mixture containing, for example, a rubber material (e.g., unvulcanized rubber material), at least one carbon material selected from carbon nanotubes and graphene, other additives, and the like.

The living body contact portion may be obtained by, for example, forming a preformed sheet-shaped material into an intended shape by using a mold or the like or by blasting, such as shot blasting, sand blasting, and liquid blasting.

Use of Biological Electrode

The biological electrode is used as, for example, an electrode of a biological measuring device for measuring biosignals, such as brainwaves, heart rate, and pulse.

Specifically, the biological electrode is used as, for example, 1) a brainwave measuring biological electrode to be inserted to the ear canal of the ear of a living body (e.g., human body), 2) a brainwave measuring biological electrode to be installed into an ear hook, 3) a brainwave measuring biological electrode to be attached to the forehead of the head or the entire head of a living body (e.g., human body), 4) a pulse measuring electrode (or heart rate measuring electrode) to be attached to the arms, the legs, the chest, or the abdomen of a living body (e.g., human body), or the like.

Biosignal Measuring Device

A biosignal measuring device according to an exemplary embodiment is a device for measuring biosignals and includes the electrode according to the exemplary embodiment.

Figure 3:
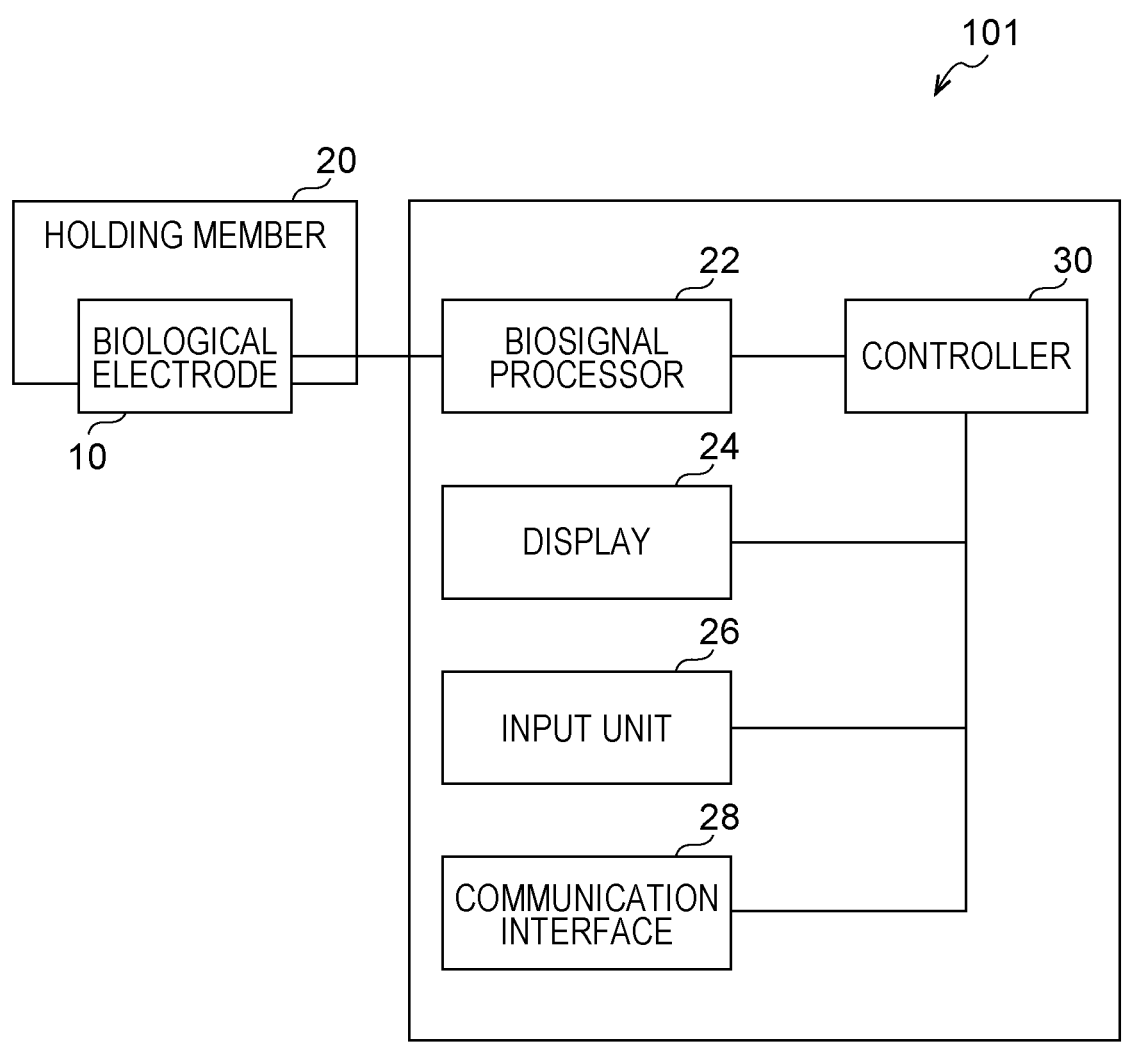
FIG. 3 is a block diagram of one example of a biosignal measuring device according to an exemplary embodiment.

For example, as illustrated in FIG. 3, a biosignal measuring device 101 according to an exemplary embodiment includes an electrode 10, a holding member 20 which holds the electrode 10, a biosignal processor 22 which processes biosignals (e.g., signals such as brainwaves, heart rate, and pulse) from a living body received by the electrode 10, a display 24 which displays various kinds of information including information about biosignals, an input unit 26 through which a user inputs operation information or the like to the biosignal measuring device 101, a communication interface 28 which transmits the processed signals to an external device, and a controller 30 which controls each unit of the device 101.

The holding member 20 is a member having a shape in accordance with the application including, for example, a brainwave measuring electrode to be inserted to the ear canal of the ear of a living body (e.g., human body), a brainwave measuring electrode to be installed into an ear hook, a brainwave measuring electrode to be attached to the forehead of the head or the entire head of a living body (e.g., human body), a pulse measuring electrode (or heart rate measuring electrode) to be attached to the arms, the legs, the chest, or the abdomen of a living body (e.g., human body), or the like.

The biosignal processor 22 includes, for example, various types of processing circuits, such as a signal amplifying circuit.

The display 24 is composed of, for example, a liquid crystal display or the like. The display 24 may have a tough panel and may function as the input unit 26.

The input unit 26 includes various input devices, such as a pointing device (e.g., mouse), a keyboard, and a button.

The communication interface 28 communicates with an external device (a personal computer for measuring biosignals, a mobile terminal) and uses, for example, standards, such as Ethernet (registered trademark), FDDI, and Wi-Fi (registered trademark).

The controller 30 includes, although not shown in the figure, a central processing unit (CPU), a read-only memory (ROM), a random access memory (RAM), a storage, and an input/output (I/O) interface. These components are communicatively coupled to each other via a bus.

The CPU, which is a central processing unit, executes various programs and controls each component. In other words, the CPU reads programs from the ROM or the storage and executes the programs using the RAM as a work area. The CPU controls each of the above components and executes various types of arithmetic processing in accordance with the programs recorded in the ROM or the storage.

The ROM stores various programs and various data. The RAM functions as a work space and temporarily stores programs or data.

The storage is composed of a hard disk drive (HDD), a solid state drive (SSD), or a flash memory and stores various programs including an operating system and various data.

The biosignal measuring device according to the exemplary embodiment may have any structure and has a structure according to biosignals to be measured. The biosignal measuring device may be a terminal device that does not display information about measured biosignals and that transmits the measured biosignals only to external devices.

Examples of the biosignal measuring device according to the exemplary embodiment include 1) a brainwave measuring device that includes a measuring unit having a biological electrode and that is to be inserted to the ear canal of the ear of a living body (e.g., human body), 2) a brainwave measuring device that includes an ear hook-shaped measuring unit having a biological electrode, 3) a brainwave measuring device that includes a measuring unit having a biological electrode and that is to be attached to the forehead of the head or the entire head of a living body (e.g., human body), and 4) a pulse measuring device (or heart rate measuring device) that includes a biological electrode and that is to be attached to the arms, the legs, the chest, or the abdomen of a living body (e.g., human body).

The biosignal measuring device according to the exemplary embodiment is suitable for a brainwave measuring device that measures brainwaves as biosignals since the biosignal measuring device according to the exemplary embodiment has good shape conformability to living bodies and accurately measures biosignals.

Next, the structure of an earphone device to be inserted into the ear to measure biosignals will be described as an example of the biosignal measuring device according to the exemplary embodiment.

The biosignal measuring device according to the exemplary embodiment may include: an insertion portion that is to be inserted into a user's ear and includes a first electrode for measuring biosignals; and an ear hook that is to be hooked over the ear, is connected to the insertion portion, and has a second electrode for measuring biosignals. At least one of the first electrode and the second electrode is the electrode according to the exemplary embodiment.

In the ear hook connected to the insertion portion, the ear hook may be connected to the insertion portion directly or with other member interposed therebetween.

A specific example of the earphone device according to the exemplary embodiment will be described below.

Figure 4:
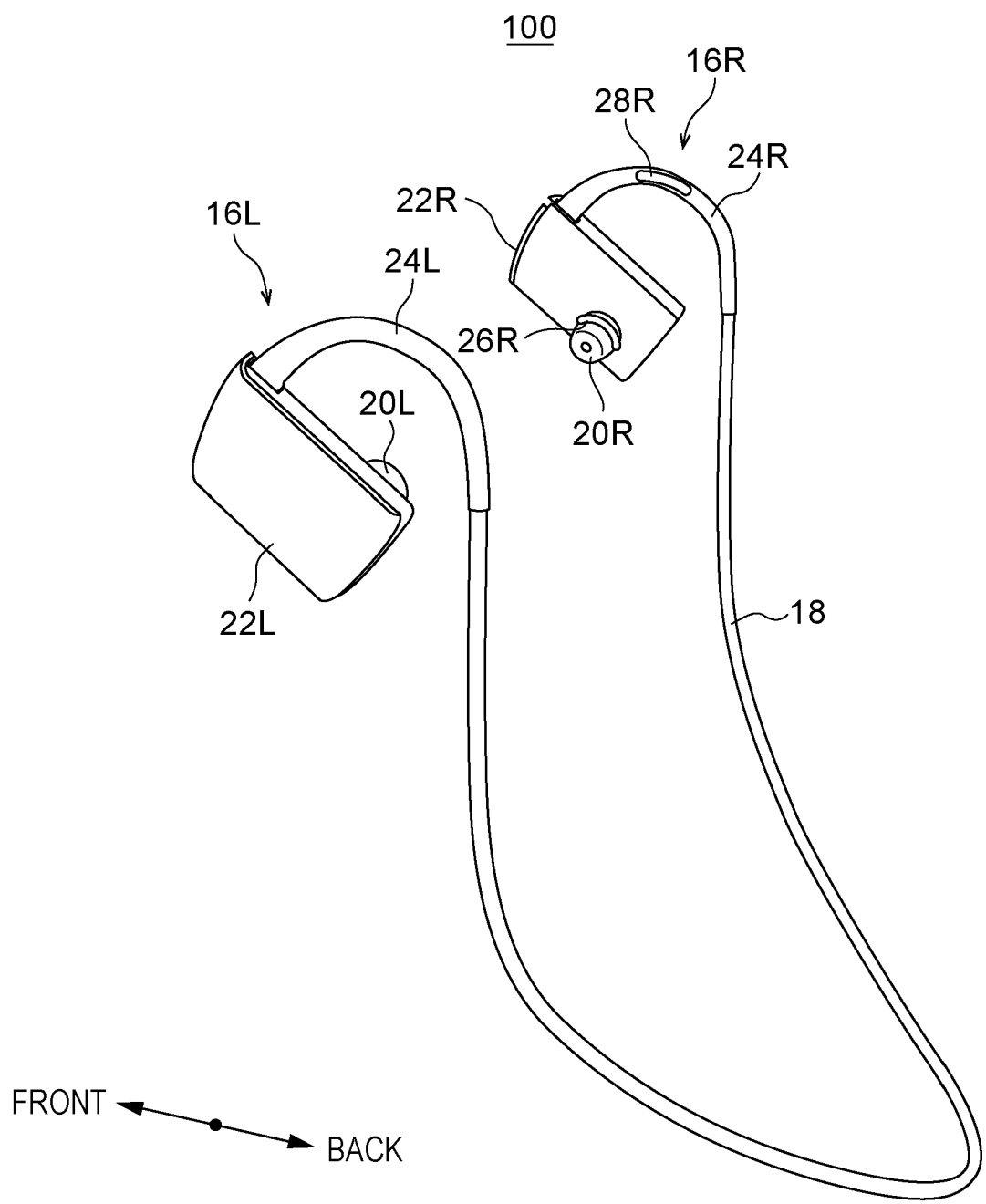
FIG. 4 is a perspective view of the general structure of an earphone device, which is an example of the biosignal measuring device according to the exemplary embodiment.
Figure 5:
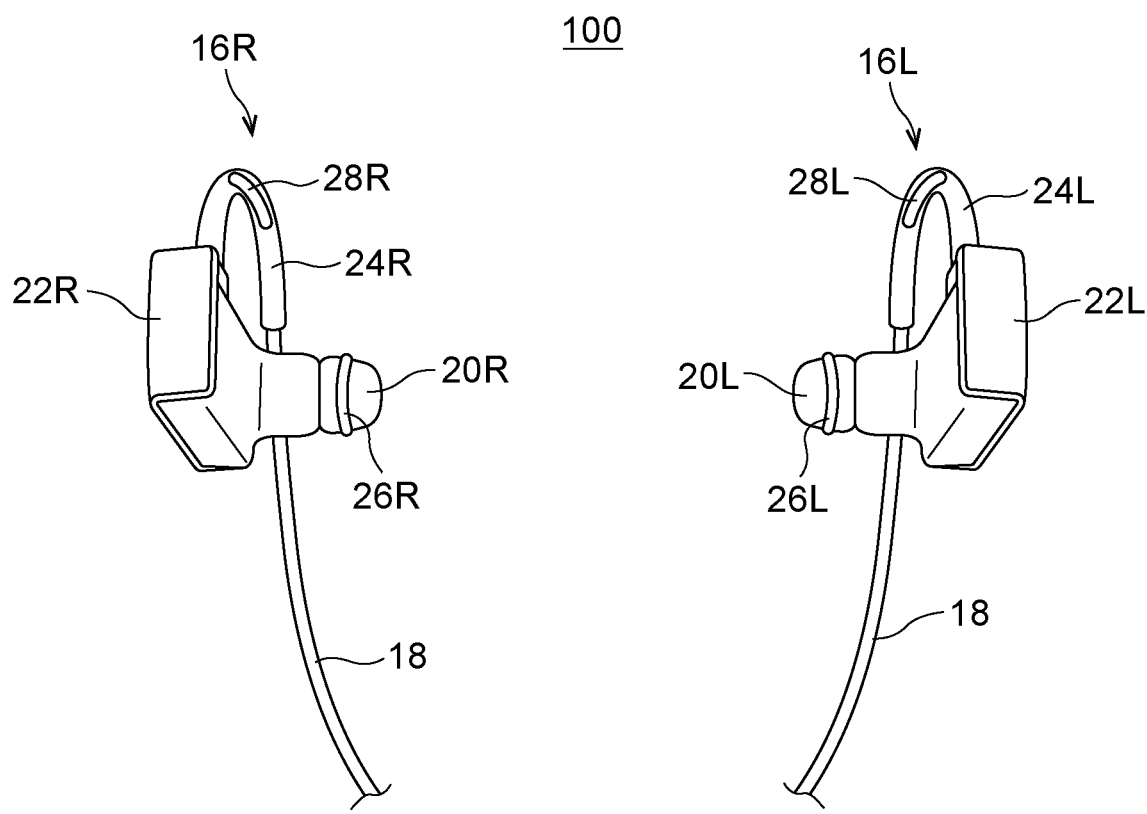
FIG. 5 is a perspective view of a partial structure of the earphone device, which is an example of the biosignal measuring device according to the exemplary embodiment.

As illustrated in FIG. 4 and FIG. 5, an earphone device 100 has earphones to be fitted to the user's ears and includes a left earphone 16L to be fitted to the user's left ear, a right earphone 16R to be fitted to the user's right ear, and a cable 18 which connects the left earphone 16L and the right earphone 16R.

The structure of the left earphone 16L will be specifically described below as an example of the earphones of the earphone device 100.

The left earphone 16L includes a left speaker 20L to be inserted into the user's left ear hole (ear canal), a left support section 22L (left base section) which supports a left speaker 20L, and a left ear hook 24L (an example of the "ear hook") which has one end connected to the left earphone 22L.

The left ear hook 24L has a second electrode, and the second electrode may be the electrode according to the exemplary embodiment.

The left speaker 20L includes a driver unit which generates sounds, a sound conduit, an equalizer, a housing (e.g., frame or housing), and an ear pad 26L (earpiece, that is, an example of the "insertion portion") which covers a section to be inserted into the ear.

The ear pad 26L has a first electrode, and the first electrode may be the electrode according to the exemplary embodiment. When the first electrode is the electrode according to the exemplary embodiment, the ear pad 26L may function as, for example, a brainwave sensor (hereinafter referred to as a "first left brainwave sensor) which detects user's brainwaves.

The left support section 22L has, for example, a thin rectangular parallelepiped shape. The left support section 22L has a surface that has the left speaker 20L and that faces the user's left ear when the user wears the earphone device 100. The left support section 22L is, for example, a case and contains a component such as an electronic board.

The left ear hook 24L is a member that generally has a curved shape and is hooked over the user's left ear when the user wears the earphone device 100. One end of the left support section 24L is connected to the front part of the left support section 22L. The left ear hook 24L curves from the junction toward the back side of the left support section 22L to form a curved section. The curved section is hooked over the left ear. The other end of the left ear hook 24L is connected to one end of the cable 18.

The surface of the left ear hook 24L has a second electrode along the left ear hook 24L. The second electrode may be the electrode according to the exemplary embodiment. When the second electrode is the electrode according to the exemplary embodiment, the left ear hook 24L may function as, for example, a brainwave sensor (hereinafter referred to as a "second left brainwave sensor) which detects user's brainwaves.

A second left brainwave sensor 28L is disposed, for example, on a surface of the left ear hook 24 L that faces the user's ear so that the second left brainwave sensor 28L contacts the left ear, more specifically, the back side of the left ear (the position closer to the skull) when the left ear hook 24L is hooked over the left ear. The second left brainwave sensor 28L disposed so as to contact the back side of the left ear detects a potential at a position closer to the brain, which can improve the accuracy of brainwave measurement. The second left brainwave sensor 28L is used as an electrode that detects the potential of the head. For example, the potential detected by the second left brainwave sensor 28L is used as a reference potential, and the ear pad 26 L serving as a first left brainwave sensor measures a potential (potential difference) from the reference potential.

The second left brainwave sensor 28L may be a member different from the left ear hook 24L and disposed at the left ear hook 24L, or the left ear hook 24L may be composed generally of the second left brainwave sensor 28L (i.e., the electrode according to the exemplary embodiment).

When the left ear hook 24L is hooked over the left ear and the left speaker 20L is inserted into the left ear's hole (ear canal), the left ear is sandwiched between the ear pad 26L serving as the first left brainwave sensor disposed in the left speaker 20L and the second left brainwave sensor 28L disposed in the left ear hook 24L. In this state, the brainwaves are measured by the ear pad 26L serving as the first left brainwave sensor and the second left brainwave sensor 28L.

As described above, the brainwave sensors can be fitted to the left ear when the left ear is sandwiched between the ear pad 26L serving as the first left brainwave sensor and the second left brainwave sensor 28L, resulting in high accuracy of brainwave measurement. Since the ear pad 26L is inserted into the left ear's hole (ear canal), the first left brainwave sensor deforms so as to favorably conform to the shape of the left ear's hole, which improves the accuracy of brainwave measurement.

EXAMPLES

The exemplary embodiments will be described below in more detail by way of Examples and Comparative Examples, but the exemplary embodiments are not limited to the following Examples.
Synthesis of Carbon Nanotube
Synthesis of CNT-1

A carbon nanotube is produced by thermal chemical vapor deposition (thermal CVD) which involves forming a thin film of a metal (catalyst), such as iron, on a silicon wafer, heating (baking) the thin film in a nitrogen atmosphere, and then growing a carbon nanotube by supplying a hydrocarbon at 1000° C. for a predetermined time. The carbon nanotube (hereinafter also referred to as "CNT-1") is obtained at a growth time (the time for supplying a hydrocarbon) of 1 hour. The average length and diameter of CNT-1 are 100 μm and 0.02 μm, respectively, as measured by the method described above.
Synthesis of CNT-2

CNT-2 is produced by the same method as in the synthesis of CNT-1 except that the growth time is 2 hours. The average length and diameter of CNT-2 are 120 μm and 0.02 μm, respectively, as measured by the method described above.
Synthesis of CNT-3

CNT-3 is produced by the same method as in the synthesis of CNT-1 except that the growth time is 3 hours. The average length and diameter of CNT-3 are 140 μm and 0.02 μm, respectively, as measured by the method described above.

Example 1

Production of Earpiece 1

The following raw materials are used: 50 parts by mass of polyether polyol (ACTOCOL ED-37B available from Mitsui Takeda Chemicals Inc., trade name "ACTOCOL ED-28"); 50 parts by mass of polymer polyol (available from Mitsui Takeda Chemicals Inc., trade name "POP-24/30"); 2.5 part by mass of trimethylolpropane; 5.6 parts by mass of dimethylpolysiloxane (available from GE Silicones, trade name "Niax Silicone L5614"); 10 parts by mass of carbon nanotube ("CNT-1" described above); and 20 parts by mass of carbodiimide-modified MDI (available from Nippon Polyurethane Industry Co., Ltd., trade name "Millionate MTL-S").

The above raw materials are mixed by mechanical frothing. Specifically, a nitrogen gas, which is an inert gas, is finely dispersed in the above raw materials by blowing 5 to 500 ml nitrogen gas per 100 ml raw materials with the raw materials stirred at a rate of 1000 rpm, whereby a foamed raw material dispersion is produced. Furthermore, 5 parts by mass of iron acetylacetate is added. Subsequently, the resulting raw material is poured into an earpiece mold and subjected to dielectric heating in two steps. In the first step, the frequency at high frequency is set to 45 MHz, and the length is 1000 mm. In the second step, the frequency at high frequency is set to 30 MHz, and the length is 2000 mm. At a line speed of 5 m/min, dielectric heating in the first step and the subsequent dielectric heating in the second step are performed to cause reaction and curing of the raw material. The resulting polyurethane foam is then cured with heat in such a manner that the polyurethane foam is heated for 2 minutes by passing it through a 10-m heating zone heated at 110° C. Moreover, in post-heating, the polyurethane foam is placed in a heating furnace and heated at 110° C. for 4 hours to produce an earpiece 1. The produced earpiece 1 is evaluated by the following evaluation method. The results are shown in Table 1.

Evaluation

Evaluation of Shape Conformability
Brainwave Measurement

The electrodes according to Examples 1 to 7 and Comparative Examples 1 to 3 are inserted into the ear canal of the ear of each of 5 subjects (a to e), and the brainwaves of each subject at rest and during walking at 5 km per hour are measured for 1 minute. Table shows the results of detection of brainwaves from the subjects. The evaluation criteria are as described below.
A: The electrode can continuously measure brainwaves for 1 minute.
B: The electrode cannot continuously measure brainwaves but can measure them after being reinserted (the electrode is resistant to practical use).
C: The electrode cannot measure brainwaves even after being reinserted (the electrode is not resistant to practical use).
Evaluation of Accuracy of Biosignal Measurement The accuracy of biosignal measurement is evaluated in the following manner using the obtained biological electrode (e.g., "earpiece 1" in Example 1). Since the a brainwaves have specific peaks in the frequency range of 8 Hz to 14 Hz, an AC voltage signal of 10 Hz is sent to the biological electrode, and a difference in AC voltage signal between input and output is evaluated. The input (reference) AC voltage signal is measured not via the biological electrode.

MindWave Mobile available from NeuroSky, Co., Ltd. is connected to a function generator (33120A 15 MHz Function/Arbitrary Waveform Generator available from Hewlett-Packard Company) without the biological electrode interposed therebetween.

Regarding the connection method, the function generator is connected to the input side of MindWave Mobile via a crocodile clip so as to enable connection with the electrode, and the REF and GND from MindWave Mobile available from NeuroSky, Co., Ltd. are each connected to the function generator via crocodile clips in such a manner that the terminals of the crocodile clips are positioned on the output side.

The reference waveform is measured by generating an AC voltage signal of 10 μV and 10 Hz from the function generator, and the waveform data is inputted to a PC. Next, the biological electrode is connected between the output side of the function generator and MindWave Mobile available from NeuroSky, Co., Ltd., and the waveform of the biological electrode is measured by generating an AC voltage signal of 10 μV and 10 Hz from the function generator. At this time, the interval between the crocodile clips connected to the biological electrode is 10 mm. The difference between the presence and the absence of the biological electrode is evaluated on the basis of the percentage difference between the mean of peak values for 50 cycles (one peak value for each cycle) of the voltage waveform during connection with the biological electrode and the mean of peak values for 50 cycles (one peak value for each cycle) of the reference voltage waveform.

The difference between the presence and the absence of the biological electrode is on the basis of the following criteria.

A: The percentage difference between the mean during connection with the biological electrode and the mean in reference is within ±0.5%.

B: The percentage difference between the mean during connection with the biological electrode and the mean in reference is within ±1.0%.

C: The percentage difference between the mean during connection with the biological electrode and the mean in reference is within ±1.5%.

D: The percentage difference between the mean during connection with the biological electrode and the mean in reference is out of ±1.5.

Examples 2 to 7, Comparative Examples 1 to 3

Production of Earpiece 2

Various earpieces are obtained by producing earpieces in the same manner as in Example 1 except that the type and amount (parts) of carbon material are changed according to Table 1. The obtained earpieces are used as electrodes, and the values of the physical properties of the earpieces are measured and evaluated in the same manner as in Example 1. The results are shown in Table 1.

TABLE 1

| | Carbon Material (Type) | Amount of Carbon Material (Relative to Rubber Material) | Surface Resistivity ($\Omega/\square$) | Volume Resistivity ($\Omega$cm) | Ratio of [Volume Resistivity/ Surface Resistivity] | 25% Compression Hardness | Evaluation | a | b | c | d | e | Evaluation of Accuracy of Biosignal Measurement |
|---|---|---|---|---|---|---|---|---|---|---|---|---|---|
| Example 1 | CNT-1 | 14 parts by mass | $8.5 \times 10^2$ | $1. \times 10^3$ | 1.2 | 65 | at rest during walking | B B | A A | A A | A B | A A | B |
| Example 2 | CNT-2 | 15 parts by mass | $7 \times 10^2$ | $1 \times 10^3$ | 1.4 | 60 | at rest during walking | A B | A A | A A | A B | A A | B |
| Example 3 | CNT-3 | 15 parts by mass | $5 \times 10^2$ | $1 \times 10^3$ | 2 | 57 | at rest during walking | A A | A A | A A | A B | A A | A |
| Example 4 | Graphene 1 | 15 parts by mass | $3 \times 10^2$ | $2 \times 10^3$ | 6 | 55 | at rest during walking | A A | A A | A A | A B | A A | A |
| Example 5 | Graphene 2 | 15 parts by mass | $4 \times 10^2$ | $2 \times 10^3$ | 5 | 52 | at rest during walking | A A | A A | A A | A A | A | A |
| Example 6 | CNT-2 | 20 parts by mass | $3 \times 10^2$ | $7 \times 10^2$ | 2.3 | 65 | at rest during walking | B B | A A | A A | A A | A | A |
| Example 7 | Graphene 2 | 3 parts by mass | $1 \times 10^5$ | $7 \times 10^6$ | 70 | 35 | at rest during walking | B B | A A | B B | B B | A A | B |
| Comparative Example 1 | Carbon black (FX-35: Denka Company Limited) | 14 parts by mass | $4 \times 10^4$ | $4.5 \times 10^4$ | 1.1 | 55 | at rest during walking | C C | B B | C C | C C | B C | D |
| Comparative Example 2 | CNT-1 | 23 parts by mass | $4 \times 10^2$ | $4.5 \times 10^2$ | 1.1 | 85 | at rest during walking | A C | A B | A C | A C | A C | B |
| Comparative Example 3 | Graphene 1 | 25 parts by mass | $3 \times 10^2$ | $3 \times 10^2$ | 1 | 90 | at rest during walking | A C | A C | A C | A C | A C | B |

The results shown in Table 1 indicate that the electrodes according to Examples have good shape conformability and accurately measure biosignals compared with the electrodes according to Comparative Examples.

The details of CNT and graphene used in each example are as described below.

Graphene 1: "Graphene Nanoplatelets": graphene, available from Sigma-Aldrich Corporation, (particle size: 5 μm, average thickness: 15 nm, surface area: 50 to 80 m$^2$/g)

Graphene 2: "Graphene Nanoplatelets": graphene, available from Sigma-Aldrich Corporation, (particle size: 25 μm, average thickness: 7 nm, surface area: 120 to 150 m$^2$/g)

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An electrode comprising:
   a living body contact portion that is to be in contact with a living body and contains a rubber material and at least one carbon material selected from carbon nanotubes and graphene,
   wherein a ratio of a volume resistivity of the living body contact portion to a surface resistivity of the living body contact portion is 1.2 or more, and
   wherein an amount of the carbon material in the living body contact portion is 3 parts by mass or more and 20 parts by mass or less relative to 100 parts by mass of the rubber material, or the living body contact portion has a 25% compression hardness of 20 kPa or more and 110 kPa or less.

2. The electrode according to claim 1, wherein the amount of the carbon material in the living body contact portion is 5 parts by mass or more and 15 parts by mass or less relative to 100 parts by mass of the rubber material.

3. The electrode according to claim 1, wherein the ratio of the volume resistivity of the living body contact portion to the surface resistivity of the living body contact portion is 1.5 or more.

4. The electrode according to claim 1, wherein the living body contact portion has a 25% compression hardness of 35 kPa or more and 65 kPa or less.

5. The electrode according to claim 1, wherein the living body contact portion is made of foam containing the rubber material and the carbon material.

6. The electrode according to claim 1, wherein the living body is an ear.

7. A biosignal measuring device for measuring biosignals, the device comprising:
   the electrode according to claim 1.

8. A biosignal measuring device for measuring biosignals, the device comprising:
   an insertion portion that is to be inserted into a user's ear and includes a first electrode for measuring biosignals, and
   an ear hook that is to be hooked over the ear, is connected to the insertion portion, and has a second electrode for measuring biosignals,
   wherein at least one of the first electrode and the second electrode is the electrode according to claim 1.

9. The biosignal measuring device according to claim 7, wherein the biosignals are brainwaves.

10. The biosignal measuring device according to claim 8, wherein the biosignals are brainwaves.

11. The electrode according to claim 1, wherein the living body contact portion has a surface layer to be in contact with the living body and a base layer in contact with the surface layer, and the surface layer has a larger carbon material content than the base layer.

* * * * *